US00PP18016P2

(12) United States Plant Patent
Strode

(10) Patent No.: US PP18,016 P2
(45) Date of Patent: Sep. 11, 2007

(54) ***SYNGONIUM* PLANT NAMED 'CONFETTI'**

(50) Latin Name: *Syngonium podophyllum*
Varietal Denomination: Confetti

(75) Inventor: Randall E. Strode, Longwood, FL (US)

(73) Assignee: Agri-Starts, Inc., Apopka, FL (US)

( * ) Notice: Subject to any disclaimer, the term of this patent is extended or adjusted under 35 U.S.C. 154(b) by 0 days.

(21) Appl. No.: 11/351,848

(22) Filed: Feb. 10, 2006

(51) Int. Cl.
*A01H 5/00* (2006.01)

(52) U.S. Cl. ..... Plt./374

(58) Field of Classification Search ..... Plt./374
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Syngonium* plant named 'Confetti', characterized by its upright and symmetrical plant shape; freely branching growth habit; dense and bushy plant form; and light green-colored leaves with random bright pink-colored splashes, flecks and spots.

2 Drawing Sheets

Botanical designation: *Syngonium podophyllum.*
Cultivar denomination: 'Confetti'.

BACKGROUND OF THE INVENTION

The present Invention relates to a new and distinct cultivar of *Syngonium* plant, botanically known as *Syngonium podophyllum* and hereinafter referred to by the name 'Confetti'.

The new *Syngonium* is a naturally-occurring whole plant mutation of the *Syngonium podophyllum* cultivar Regina Red, not patented. The new *Syngonium* was discovered and selected by the Inventor on Jun. 6, 2003 in a controlled environment in Apopka, Fla. from within a population of plants of 'Regina Red'.

Asexual propagation of the new cultivar by tissue culture since June, 2003, in a controlled environment in Apopka, Fla. has shown that the unique features of this new *Syngonium* are stable and reproduced true to type in successive generations.

SUMMARY OF THE INVENTION

The following traits have been repeatedly observed and are determined to be the unique characteristics of 'Confetti'. These characteristics in combination distinguish 'Confetti' as a new and distinct cultivar of *Syngonium:*

1. Upright and symmetrical plant shape.
2. Freely branching growth habit; dense and bushy plant form.
3. Light green-colored leaves with random bright pink-colored splashes, flecks and spots.

In side-by-side comparisons conducted by the Inventor in Apopka, Fla., plants of the new *Syngonium* differed primarily from plants of the parent, the cultivar Regina Red, in leaf color as plants of the cultivar Regina Red had solid pink-colored leaves.

Plants of the new *Syngonium* can be compared to plants of the cultivar Pink Splash, not patented. In side-by-side comparisons conducted in Apopka, Fla., plants of the new

*Syngonium* differed primarily from plants of the *Syngonium* cultivar Pink Splash in leaf color as plants of the cultivar Pink Splash had green-colored leaves with random pink-colored splashes, flecks and spots.

BRIEF DESCRIPTION OF THE PHOTOGRAPHS

The accompanying colored photographs illustrate the overall appearance of the new *Syngonium,* showing the colors as true as it is reasonably possible to obtain in colored reproductions of this type. Colors in the photographs may differ slightly from the color values cited in the detailed botanical description which accurately describe the colors of the new *Syngonium.*

The photograph on the first sheet comprises a side perspective view of a typical plant of 'Confetti' grown in a container.

The photograph at the top of the second sheet is a close-up view of the upper surface of the typical leaf of 'Confetti'.

The photograph at the bottom of the second sheet is a close-up view of the lower surface of a typical leaf of 'Confetti'.

DETAILED BOTANICAL DESCRIPTION

The cultivar Confetti has not been observed under all possible environmental conditions. The phenotype may vary somewhat with variations in environment such as temperature and light intensity without, however, any variance in genotype. The following observations and measurements describe plants of the new *Syngonium* that were grown in 15-cm containers, in Sebring, Fla., in a polycarbonate-covered greenhouse with light levels about 5,000 foot-candles. During the production of the plants, day temperatures ranged from about 21° C. to about 33° C. and night temperatures ranged from about 10° C. to about 20° C. Plants used for the photographs and description were about four months from planting. Color references are made to The Royal Horticultural Society Colour Chart, 2001 Edition, except where general terms of ordinary dictionary significance are used.

Botanical classification: *Syngonium podophyllum* cultivar Confetti.

Parentage: Naturally-occurring whole plant mutation of the *Syngonium podophyllum* cultivar Regina Red, not patented.

Propagation:

*Type.*—By tissue culture.

*Time to initiate roots, summer.*—About 10 days at 29° C.

*Time to initiate roots, winter.*—About 20 days at 20° C.

*Time to produce a rooted plant, summer.*—About 70 days at 29° C.

*Time to produce a rooted plant, winter.*—About 84 days at 20° C.

*Root description.*—Thick and fleshy with fine laterals; N199D in color; root tips, 160B to 160C; strong root system.

Plant description:

*Plant form.*—Upright and symmetrical plant form; rounded inverted triangle.

*Growth habit.*—Plant size appropriate for 10-cm to 20-cm containers.

*Growth habit.*—Plants are freely clumping; usually about eight branch stems develop per plant; dense and bushy plant form. Moderately vigorous growth habit.

*Plant height.*—About 22 cm.

*Plant width* (*spread*).—About 35 cm.

*Stem description.*—Length (from soil surface to junction of the last two unrolled leaves): About 2.8 cm. Diameter: About 6 mm. Internode length: About 8 mm. Texture: Smooth, glabrous. Strength: Sturdy, flexible; upright. Color, immature: 145D. Color, mature: 147A to 147D depending on exposure to light.

*Foliage description.*—Arrangement: Alternate; simple. Length: About 13 cm. Width: About 7.5 cm. Shape: Ovate. Apex: Acuminate. Base: Sagittate. Margin: Entire; somewhat undulate. Aspect: Mostly flat; between primary veins, convex. Texture, upper and lower surfaces: Smooth, glabrous. Venation pattern: Pinnate. Color: Developing leaves, upper surface: 145B to 145C to 147D; areas along the veins, 193D; random splashes, flecks and spots, 182B to 182C; midrib, 147B. Developing leaves, lower surface: between 147D and 146C; midrib, 147D. Fully expanded leaves, upper surface: 191D flushed with 137A; areas along the veins, 192A; random splashes, flecks and spots, 182B to 182C; midrib, 147A to 147B; lateral veins, 147B to 147C. Fully expanded leaves, lower surface: 147B to 147C; midrib, 147B to 147C; lateral veins, 147C. Petiole: Length: About 15 cm. Diameter, distal: About 3 mm. Diameter, proximal: About 1.2 cm. Color: More green than 147C. Wing length: About 4.7 cm. Wing diameter: About 6 mm. Wing color, outer surface: More green than 147C to 147D. Wing color, inner surface: 147D.

Inflorescence description: Inflorescence development has not been observed on plants of the new *Syngonium.*

Disease/pest resistance: Plants of the new *Syngonium* have not been observed to be resistant to pathogens and pests common to *Syngonium.*

Temperature tolerance: Plants of the new *Syngonium* have been observed to be tolerant to temperatures ranging from about 10° C. to about 40° C.

It is claimed:

1. A new and distinct cultivar of *Syngonium* plant named 'Confetti', as illustrated and described.

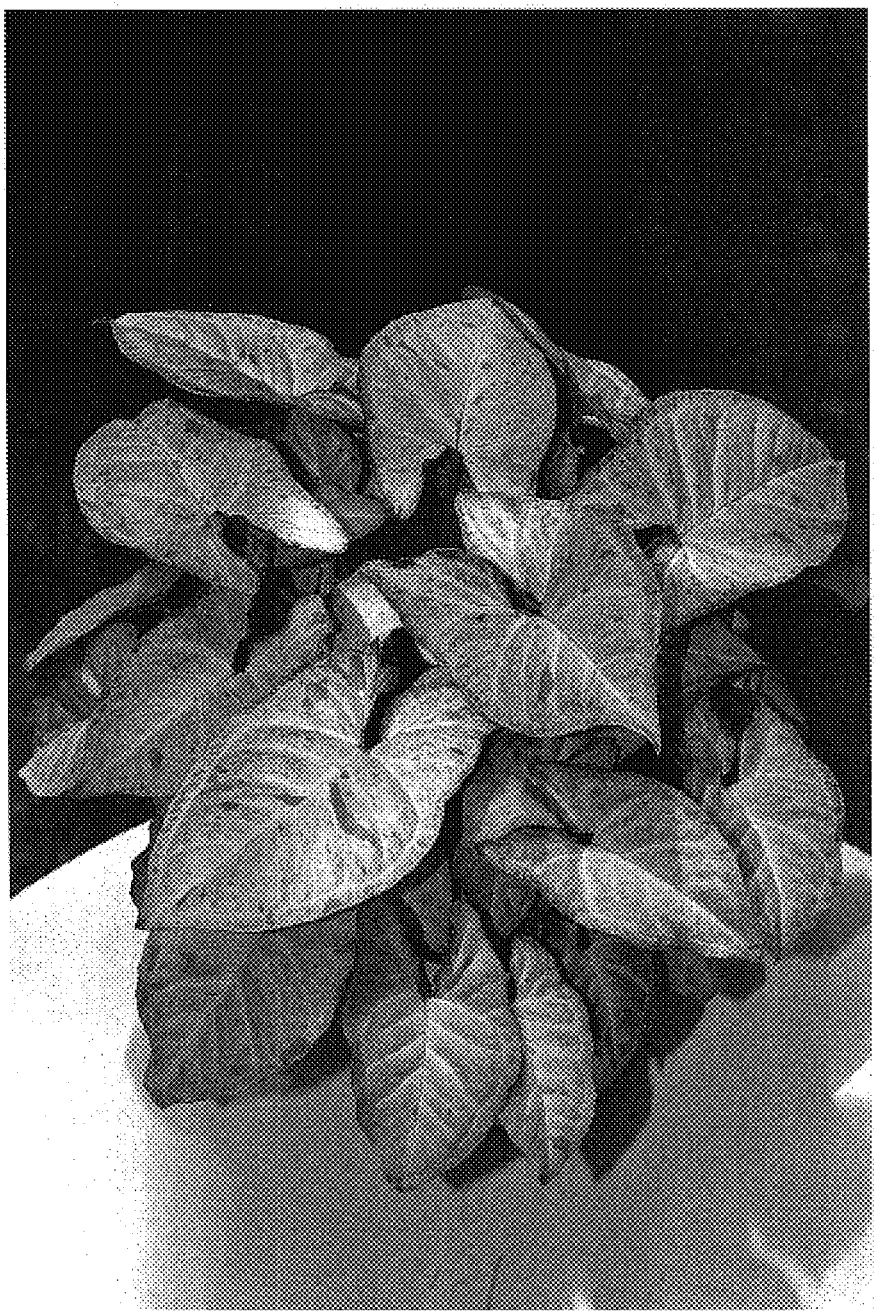

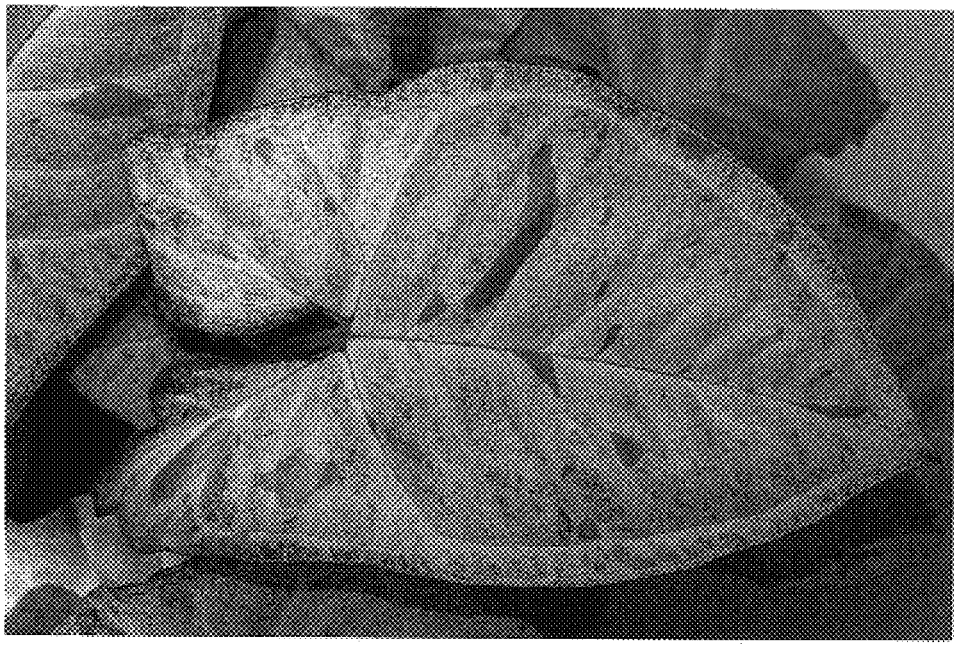
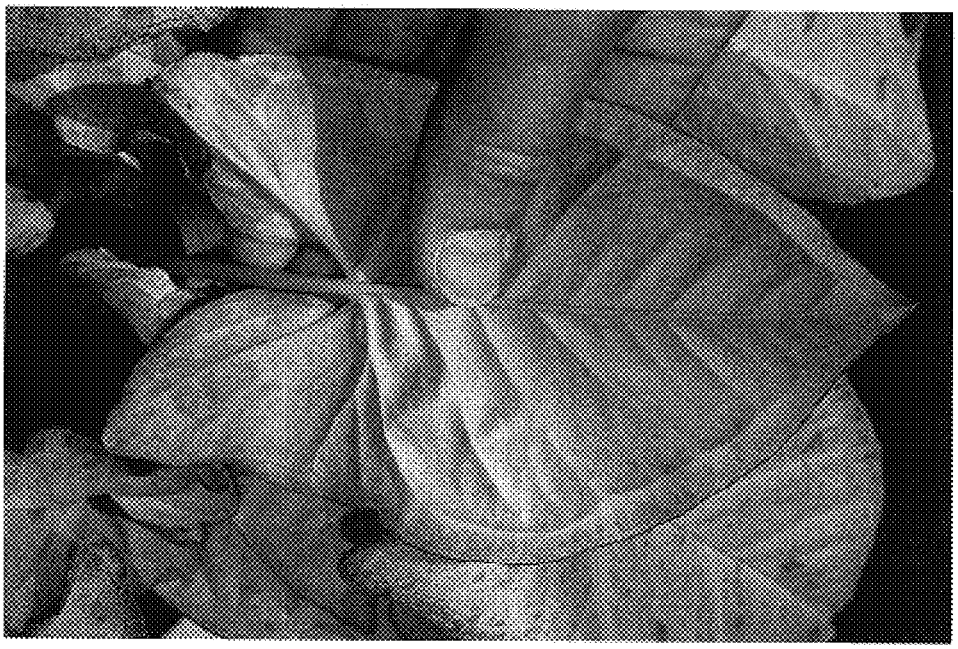

* * * * *